United States Patent
Bergel et al.

(10) Patent No.: US 10,758,501 B2
(45) Date of Patent: Sep. 1, 2020

(54) USE OF HISTONE ACETYLTRANSFERASE INHIBITOR AMIDOXIMES AS ANTI-PROLIFERATIVE AGENTS

(71) Applicant: Texas Woman's University, Denton, TX (US)

(72) Inventors: Michael Bergel, Denton, TX (US); James E. Johnson, Denton, TX (US); Debra Dolliver, Tuscaloosa, AL (US); Sudheer Dhanireddy, Denton, TX (US); Amon Gekombe, Lewisville, TX (US)

(73) Assignee: Texas Woman's University, Denton, TX (US)

( * ) Notice: Subject to any disclaimer, the term of this patent is extended or adjusted under 35 U.S.C. 154(b) by 0 days.

(21) Appl. No.: 16/149,892

(22) Filed: Oct. 2, 2018

(65) Prior Publication Data

US 2019/0167608 A1    Jun. 6, 2019

Related U.S. Application Data

(60) Provisional application No. 62/567,089, filed on Oct. 2, 2017.

(51) Int. Cl.
*A61K 31/15* (2006.01)
*A61K 33/243* (2019.01)
*A61P 35/00* (2006.01)

(52) U.S. Cl.
CPC ............ *A61K 31/15* (2013.01); *A61K 33/243* (2019.01); *A61P 35/00* (2018.01)

(58) Field of Classification Search
None
See application file for complete search history.

(56) References Cited

PUBLICATIONS

MedicineNet, "Definition of Cancer", https://www.medicinenet.com/script/main/art.asp?articlekey=2580, 1 page; downloaded Mar. 2, 2020.*
Bergel et al. (2000), Acetylation of novel sites in the nucleosomal binding domain of chromosomal protein HMG-14 by p300 alters its interaction with nucleosomes. J. Biol. Chem., 275(15):11514-11520.
Dekker et al. (2009) Histone acetyl transferases as emerging drug targets. Drug Discov. Today, Oct. 14, 2009 (19-20):942-8. Epub Jul. 2, 2009.
Dokmanovic et al. (2007) Histone deacetylase inhibitors: overview and perspectives. Mol Cancer Res., 5 (10):981-9.
Eliseeva et al. (2007) Characterization of novel inhibitors of histone acetyltransferases. Mol Cancer Ther, 6 (9), 2391-8.
Herrera et al. (1997) The histone acetyltransferase activity of human CGN5 and PCAF is stabilized by coenzymes. J. Biol. Chem., 272(43), 27253-27258.
Johnson et al. "Bisamidoximes: Synthesis and Complexation with Iron (III)." Aust. J. Chem. 2007, 60, 685-690.
Lim et al. (2005) Chromosomal protein HMGN1 enhances the acetylation of lysine 14 in histone H3. The EMBO J. 24, 3038-3048.
Liu et al. (2008) The structural basis of protein acetylation by the p300/CBP transcriptional coactivator. Nature 451 (7180), 486-50.
Morimoto et al. (2008) The dietary compound curcumin inhibits p300 histone acetyltransferase activity and prevents heart failure in rats. J Clin. Invest, 118 (3): 868-878.
Piaz et al. (2011) Chemical Biology of histone acetyltransferase natural compounds modulators, Mol. Divers. 15:401-416.
Wapenaar et al. Histone acetyltransferases: challenges in targeting bi-substrate enzymes (2016) Clinical Epigenetics 8:59, DOI 10.1186/s13148-016-0225-2.
Wolffe Chromatin remodeling: why it is important in cancer, (2001) Oncogene 20 (24), 2988-2990.
Yang et al. (2013) Small-Molecule Inhibitors of acetyltransferase p300 identified by high-throughput screening are potent anticancer agent. Mol. Cancer Ther; 12 (5) 610-620.
Yoshida et al. (2001) Histone deacetylase as a new target for cancer chemotherapy, Cancer Chemother Pharmacol 48 (Suppl 1); S20-S26.
Gekombe et al. Novel amidoximes induce core histone hypoacetylation prior to apoptosis in colon carcinoma cells. TWU Student Creative Arts and Research Symposium, Denton, Texas, Poster presentation, Apr. 2014.
Dhanireddy et al. "Novel Amidoximes Induce Apoptosis and Decrease Histone Acetylation in Colon Carcinoma and Inhibit p300 In Vitro", Experimental Biology, 2011 National Conference, Washington D.C., Poster and Abstract accepted, Apr. 2011.
Gekombe et al. "Toxicity studies of novel potential anti-cancer amidoximes in BALB/c mice" Texas Woman's University Creative Arts and Research Symposium. Denton, TX. Poster Presentation, Apr. 2016.
Dhanireddy et al. "Inhibition of cell proliferation by novel amidoximes involves decreased histone acetylation" TWU 11th Student Creative Arts and Research Symposium, Poster and Abstract, 2008.
Dhanireddy et al. "Inhibition of cell proliferation by novel amidoximes involves decreased histone acetylation and p300 inhibition" TWU 12th Student Creative Arts and Research Symposium, Poster Presentation, 2009.
Gekombe et al. "Novel amidoximes inhibit proliferation of murine mammary carcinoma cell lines" Texas Woman's University Creative Arts and Research Symposium. Denton, TX. Poster Presentation, Apr. 2015.
Dhanireddy et al. "Induction of Apoptosis by Novel Amidoximes Involves Decreased Histone Acetylation and p300 Inhibition" Texas Genetics Society, 37th Annual Meeting, M.D. Anderson Cancer Center, Houston, Poster and Abstract, Apr. 2010.

* cited by examiner

*Primary Examiner* — Savitha M Rao
*Assistant Examiner* — Gregg Polansky
(74) *Attorney, Agent, or Firm* — Kowert, Hood, Munyon, Rankin & Goetzel, P.C.; Mark R. DeLuca

(57) ABSTRACT

Described herein is the use of bisamidoximes compounds for the treatment of cancer. In preferred embodiments, combinations of two or more bisamidoximes or combinations of a bisamidoxime and another anti-cancer agent were found to be effective against various types of cancer cells.

16 Claims, 4 Drawing Sheets

USE OF HISTONE ACETYLTRANSFERASE INHIBITOR AMIDOXIMES AS ANTI-PROLIFERATIVE AGENTS

PRIORITY CLAIM

This application claims priority to U.S. Provisional Application Ser. No. 62/567,089 entitled "USE OF HISTONE ACETYLTRANSFERASE INHIBITOR AMIDOXIMES AS ANTI-PROLIFERATIVE AGENTS" filed Oct. 2, 2017, which is incorporated herein by reference in its entirety.

BACKGROUND OF THE INVENTION

1. Field of the Invention

The invention generally relates to use of bisamidoximes for the treatment of cancer.

2. Description of the Relevant Art

Lung cancer, breast cancer, and colon cancer are three types of common cancer, which are estimated to be among the top four causes of cancer-related deaths during 2017. For instance, in 2017, it is estimated that 255,180 new cases of breast cancer will be diagnosed in the USA (in women and men), and 41,070 breast cancer patients will die, making it the most common cancer diagnosed, and the fourth deadliest cancer.

In the cell, the long double-helical DNA strands are packed into a complex structure associated with various proteins and RNA. This structure, named chromatin, is folded into several levels. Each level of folding increases the compactness and tightness of the packed DNA. Unfolding of this tightly packed chromatin is important for all DNA-mediated functions, such as producing RNA transcripts (transcription), replicating new DNA strands (replication), and repairing damages within the DNA. The unfolding of DNA enables the accessibility of large protein complexes that carry out these tasks. The basic repetitive packaging unit of chromatin is a beadlike core particle composed of 8 positively charged proteins, called core histones, upon which the DNA is wound approximately twice. These beads repeat themselves millions of times in the chromatin, linked by starches of DNA between each consecutive bead, in a basic form described as "beads on a string." The core particle (the bead), with the two linker DNA segments extending from it, is called a nucleosome. The width of this first basic level of chromatin fiber is 10 nm (nanometer). The negatively charged DNA is attracted to the core histones by virtue of their positive charges and by formation of hydrogen bonds.

Folding the chromatin from the 10 nm fiber to the 30 nm fiber is a dynamic and reversible process that is very accurately regulated temporally and spatially during embryonic development, during cellular growth and differentiation, and in response to environmental cues. The 30 nm chromatin fiber is a more compact form that represses the activation of genes (transcription). This transcription repression by the 30 nm fiber is crucial for regulating the normal development and activity of the cell. Some subsets of genes are activated and others are silenced in a very tightly orchestrated manner. The silencing of protein production of some genes is not less critical for the cell than the activation of others. For instance, cancer can develop when some genes, known as oncogenes, stop being repressed.

One of the major mechanisms for unfolding and folding chromatin is by acetylation and deacetylation of the tails of the core histones, respectively. Deacetylation and consequently folding of chromatin is carried out by a group of enzymes named histone deacetylases (HDACs). These HDACs are involved in removing the acetyl groups from the core histones and enabling a higher attraction between the more positively charged core histones and the DNA, which result in an increase of the compaction. There are four classes of HDACs and 11 known HDACs in the zinc-dependent HDAC classes I, II and IV. The activity of HDACs is reversed by another group of enzymes named Histone acetyltransferases (HATs), which are involved in unfolding chromatin. HATs act by adding an acetyl group to the core histones and consequently neutralizing the positive charge of the histones and alleviating the strong interaction between the negatively charged DNA and the less positively charged histones.

Figure 1:
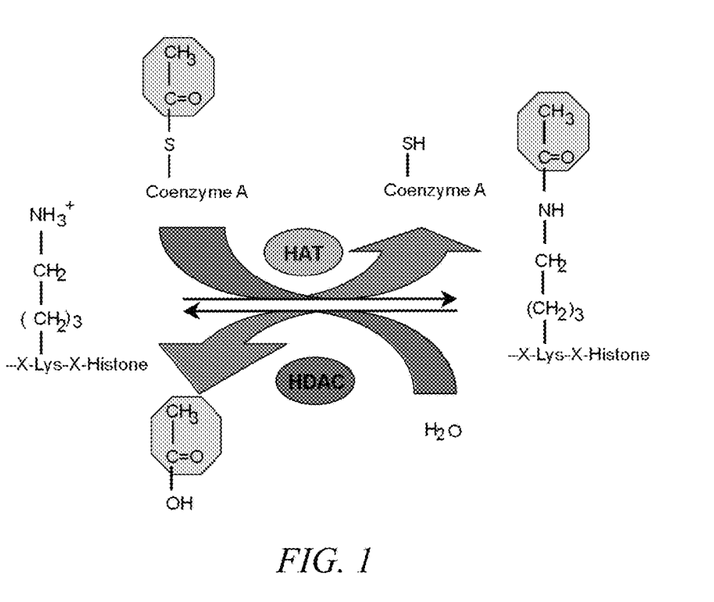
FIG. 1 depicts a schematic diagram of how the steady-state of histone acetylation is maintained by opposing activities of histone acetyltransferases and deacetylases.

FIG. 1 shows how the steady-state of histone acetylation is maintained by opposing activities of histone acetyltransferases and deacetylases. Acetylation is the transfer of the acetyl moiety from an acetyl coenzyme A donor to the side chain of a lysine residue in an acceptor protein. This is an example of a post-translational modification of a protein, since this chemical change happens in the mature protein and not as part of its synthesis. The steady state of histone acetylation is maintained by the opposing activities of two groups of enzymes, HATs, that add the acetyl group and HDACs that remove it.

In recent years, many research groups have focused their attention on the discovery of drugs that inhibit HDACs and can inhibit the growth of malignant cells. Some of these drugs are already in clinical use. Compounds that inhibit HATs were also discovered, and they, as well, caused a selective growth inhibition and death of malignant cells. Furthermore, recently there have been several reports that the dietary compound curcumin inhibits the activity of the histone acetyltransferase p300 and prevents heart failure in animals. Potential HAT malfunction related pathology has been demonstrated in a variety of diseases such as Alzheimer, diabetes, hyperlipidaemia, as well as in asthma, and COPD, making HAT inhibitors sought-after compounds. Despite the progress made in understanding the structure of HATs, such as p300, their enzymatic mechanism and the way the HATs are inhibited is essentially unclear. Also, several HAT inhibitors demonstrated reactivity, instability, low potency, and lack of selectivity between HAT subtypes and other enzymes.

There is a continuing need for new anti-cancer compounds, since the existing compounds are not curing all cases of cancer and have numerous negative side effects. Furthermore, many of the currently used chemotherapeutic agents result in a drug resistance response in patients, in which case the patient's tumors stop responding to the treatment. Histone modifiers, such as HDAC inhibitors and HAT inhibitors, are sought-after compounds, since many of them specifically target malignant cells by either suppressing oncogenes or inducing the expression of tumor-suppressor genes. Some of these compounds are already in clinical use, especially HDAC inhibitors. However, there is still a need for anti-cancer compounds exhibiting superior effectiveness while minimizing side effects associated with many anti-cancer compounds.

SUMMARY OF THE INVENTION

In an embodiment, a method of treating cancer in a subject comprises administering to a subject who would benefit from such treatment a therapeutically effective amount of a pharmaceutical composition comprising one or more bisamidoximes.

In one embodiment, one or more of the bisamidoximes have the structure:

where W: is —$(CH_2)_2$—; —$(CH_2)_3$—; —$(CH_2)_4$—; or —$(CH_2)_3$—$N(CH_3)$—$(CH_2)_3$—; and
where Y is H, $C_1$-$C_6$ alkyl, or halogen. In one embodiment, Y is methyl.

In one embodiment, one or more of the bisamidoximes are selected from the group of compounds consisting of JJMB 5, JJMB 7, and JJMB 9:

In one embodiment, the pharmaceutical composition comprises two or more bisamidoximes. The pharmaceutical composition may comprise JJMB5 and JJMB 9, JJMB5 and JJMB7, or JJMB7 and JJMB9.

In one embodiment, the cancer is breast cancer, lung cancer, or colon cancer.

In one embodiment, a method of treating cancer in a subject comprising administering to a subject who would benefit from such treatment a therapeutically effective amount of a pharmaceutical composition comprising an anticancer agent and one or more bisamidoximes. In one embodiment, the anticancer agent is cisplatin.

In one embodiment, a method of inhibiting histone acetyltransferases (HATs) in a biomedical application, comprising applying an effective amount of a composition comprising one or more bisamidoximes to a biomedical application that includes HATs.

BRIEF DESCRIPTION OF THE DRAWINGS

Advantages of the present invention will become apparent to those skilled in the art with the benefit of the following detailed description of embodiments and upon reference to the accompanying drawings in which.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

It is to be understood the present invention is not limited to particular devices or methods, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected.

The terms used throughout this specification generally have their ordinary meanings in the art, within the context of the invention, and in the specific context where each term is used. Certain terms are discussed below, or elsewhere in the specification, to provide additional guidance to the practitioner in describing the devices and methods of the invention and how to make and use them. It will be appreciated that the same thing can be said in more than one way. Consequently, alternative language and synonyms may be used for any one or more of the terms discussed herein, nor is any special significance to be placed upon whether or not a term is elaborated or discussed in greater detail herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term.

As used herein, the term "cancer" refers to a cellular disorder characterized by uncontrolled or dysregulated cell proliferation, decreased cellular differentiation, inappropriate ability to invade surrounding tissue, and/or ability to establish new growth at ectopic sites. The term "cancer"

includes, but is not limited to, solid tumors and bloodborne tumors. The term "cancer" encompasses diseases of skin, tissues, organs, bone, cartilage, blood, and vessels. The term "cancer" further encompasses primary and metastatic cancers.

The terms "cells" or "groups of cells" as used herein further encompasses cultured cells that have been explanted from a body or tissue and that have been maintained in vitro in a cell culture system. Examples of such cells include "primary cell" cultures. Primary cells are those cells that are explanted directly from a donor organism or tissue. Primary cells may typically be capable of undergoing a limited number of divisions in culture, but they generally do not continue to grow and eventually senesce and die.

Further examples of isolated cells include "secondary cell" cultures. Secondary cells are those cells that are explanted directly from a donor organism or tissue and that are maintained and propagated in culture for a protracted period of time, typically exceeding that of primary cells. Often times, secondary cells may be propagated in vitro for up to as many as 100 generations or more. Secondary cells are typically not immortalized however, and eventually undergo senescence. The number of cell divisions that secondary cells may undergo is related to their degree of differentiation. More terminally differentiated cells undergo fewer cell divisions and senesce early. Less well-differentiated cells, such as embryonic fibroblasts and cells that have begun to undergo neoplastic transformation, typically have a higher generation potential and can undergo a greater number of divisions.

Yet further examples of isolated cells include "immortalized cells." Immortalized cells may typically be maintained and propagated in vitro indefinitely as long as the correct culture conditions are maintained. Immortalized cell lines are commonly referred to in the art as "transformed cells." The growth properties of such cells are altered. Typically, such cells have undergone one or more genotypic changes, such as, for example point mutations, aneuploidy or other chromosomal alterations. Immortalized cells may or may not be cancerous or malignant. Non-malignant transformed cells typically exhibit one or more of several properties when grown in vitro. Non-limiting examples of the phenotypic properties exhibited by non-malignant transformed cells include anchorage-dependent growth, growth factor dependence, and growth-arrest under conditions of nutritional deficiency. Furthermore, while transformed cells are generally not as highly differentiated as their primary or secondary counterparts, they nonetheless typically retain at least a subset of the morphological and biochemical properties of the cell type from which they are derived. Finally, non-malignant cells exhibit a growth property known in the art as "contact inhibition." Typically, such cells will continue to grow and divide in vitro when plated at low density. When the density of cells is sufficient so that a "monolayer" of cells has formed (i.e., the borders of adjacent cells are substantially touching), growth inhibitory signals pass between the cells, the cells exit the cell cycle and cease dividing. Such "contact inhibited" cells are frequently coupled by gap junctions. Loss of contact inhibition is a widely regarded sign that cells have become cancerous or oncogenic. Such cells do not stop dividing when they form a monolayer in culture. Rather, they continue to divide and pile up on top of one another in "foci". It is generally well accepted by ordinary practitioners of the art that cells that form foci in culture are tumor cells.

As used herein, the term "neoplastic transformation" or "oncogenic transformation," generally refers to a proliferative disorder of cells characterized by one or more of several cellular changes. Such cellular changes are manifested by cells that have become, or are on the way to becoming, cancerous or malignant. Characteristics of cells that have undergone neoplastic transformation are well known to ordinary practitioners of the art and may include, but are not limited to, loss of contact inhibition, escape from control mechanisms, loss of GJIC, increased growth potential, increased growth rate, the ability to form colonies in soft agar, alterations in the cell surface, alterations in the expression of certain protein or gene markers, karyotypic abnormalities, aneuploidy, morphological and biochemical deviations from the norm, and other attributes that confer the ability of the cell or group of cells to invade, metastasize, and kill. Neoplastic transformation may be induced, at least in part, by exposure of a cell or group of cells to radiation, or to one or more oncogenic agents such as certain viruses or carcinogens. A "carcinogen" as used herein, generally refers to a substance that increases the likelihood that a cell or group of cells begins the process of neoplastic transformation. Carcinogens may include genotoxic agents, also known in the art as "mutagens", and non-genotoxic agents, which induce neoplasms by non-genomic mechanisms.

The term "apoptosis," as used herein, generally refers to a morphologically distinct form of programmed cell death that is important in the normal development and maintenance of multicellular organisms. Dysregulation of apoptosis can take the form of inappropriate suppression of cell death, as occurs in the development of cancers, or in a failure to control the extent of cell death, as is believed to occur in acquired immunodeficiency and certain neurodegenerative disorders. Apoptosis is an active process in which cells induce their self-destruction in response to specific cell death signals or in the absence of cell survival signals. It is distinct from necrosis, which is cell death occurring as a result of severe injurious changes in the environment. Apoptosis of a cell can be characterized at least by the rapid condensation of the cell with collapse of the nucleus but preservation of membranes; or, cleavage of nuclear DNA at the linker regions between nucleosomes to produce fragments which can be easily visualized by agarose gel electrophoresis as a characteristic ladder pattern. Cells undergoing apoptosis exhibit a characteristic series of morphological changes including mitochondrial membrane swelling and rupture, leakage of cytosolic contents into the surrounding area, and inflammation in tissues. The pattern of events occurring during apoptosis is orderly and includes; cell shrinkage; appearance of bubble-like blebs on their surface; degradation of chromatin (DNA in a complex with protein and RNA) in their nucleus; mitochondrial rupture and release of cytochrome c into the cytosol; breakage of the cell into small, membrane-wrapped, fragments (commonly referred to as "apoptotic bodies" or "corpses"); exposure of phosphatidylserine on the outer leaflet of the cell membrane; and recruitment of phagocytic cells like macrophages and dendritic cells which then engulf the cell fragments.

Various pathologies occur due to a defective or aberrant regulation of apoptosis in the affected cells of an organism. For example, defects that result in a decreased level of apoptosis in a tissue as compared to the normal level required to maintain the steady-state of the tissue can promote an abnormal increase of the amount of cells in a tissue. This has been observed in various cancers, where the formation of tumors occurs because the cells are not dying at their normal rate.

The terms "reducing," "inhibiting" and "ameliorating," as used herein, when used in the context of modulating a pathological or disease state, generally refers to the prevention and/or reduction of at least a portion of the negative consequences of the disease state. When used in the context of an adverse side effect associated with the administration of a drug to a subject, the term(s) generally refer to a net reduction in the severity or seriousness of said adverse side effects.

As used herein, the term "systemically," when used in the context of a physiological parameter, generally refers to a parameter that affects the entire body of a subject, or to a particular body system.

As used herein the terms "administration," "administering," or the like, when used in the context of providing a pharmaceutical or nutraceutical composition to a subject generally refers to providing to the subject one or more pharmaceutical, "over-the-counter" (OTC) or nutraceutical compositions in combination with an appropriate delivery vehicle by any means such that the administered compound achieves one or more of the intended biological effects for which the compound was administered. By way of non-limiting example, a composition may be administered parenteral, subcutaneous, intravenous, intracoronary, rectal, intramuscular, intra-peritoneal, transdermal, or buccal routes of delivery. Alternatively, or concurrently, administration may be by the oral route. The dosage administered will be dependent upon the age, health, weight, and/or disease state of the recipient, kind of concurrent treatment, if any, frequency of treatment, and/or the nature of the effect desired. The dosage of pharmacologically active compound that is administered will be dependent upon multiple factors, such as the age, health, weight, and/or disease state of the recipient, concurrent treatments, if any, the frequency of treatment, and/or the nature and magnitude of the biological effect that is desired.

As used herein, the term "treat" in the context of animals generally refers to an action taken by a caregiver that involves substantially inhibiting, slowing or reversing the progression of a disease, disorder or condition, substantially ameliorating clinical symptoms of a disease disorder or condition, or substantially preventing the appearance of clinical symptoms of a disease, disorder or condition.

As used herein, terms such as "pharmaceutical composition," "pharmaceutical formulation," "pharmaceutical preparation," or the like, generally refer to formulations that are adapted to deliver a prescribed dosage of one or more pharmacologically active compounds to a cell, a group of cells, an organ or tissue, an animal or a human. Methods of incorporating pharmacologically active compounds into pharmaceutical preparations are widely known in the art. The determination of an appropriate prescribed dosage of a pharmacologically active compound to include in a pharmaceutical composition in order to achieve a desired biological outcome is within the skill level of an ordinary practitioner of the art. A pharmaceutical composition may be provided as sustained-release or timed-release formulations. Such formulations may release a bolus of a compound from the formulation at a desired time, or may ensure a relatively constant amount of the compound present in the dosage is released over a given period of time. Terms such as "sustained release" or "timed release" and the like are widely used in the pharmaceutical arts and are readily understood by a practitioner of ordinary skill in the art. Pharmaceutical preparations may be prepared as solids, semi-solids, gels, hydrogels, liquids, solutions, suspensions, emulsions, aerosols, powders, or combinations thereof. Included in a pharmaceutical preparation may be one or more carriers, preservatives, flavorings, excipients, coatings, stabilizers, binders, nanoparticles, solvents and/or auxiliaries that are, typically, pharmacologically inert. It will be readily appreciated by an ordinary practitioner of the art that, pharmaceutical compositions, formulations and preparations may include pharmaceutically acceptable salts of compounds. It will further be appreciated by an ordinary practitioner of the art that the term also encompasses those pharmaceutical compositions that contain an admixture of two or more pharmacologically active compounds, such compounds being administered, for example, as a combination therapy.

The term "pharmaceutically acceptable salts" includes salts prepared from by reacting pharmaceutically acceptable non-toxic bases or acids, including inorganic or organic bases, with inorganic or organic acids. Pharmaceutically acceptable salts may include salts derived from inorganic bases include aluminum, ammonium, calcium, copper, ferric, ferrous, lithium, magnesium, manganic salts, manganous, potassium, sodium, zinc, etc. Examples include the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-dibenzylethylenediamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, etc.

As used herein the terms "subject" generally refers to a mammal, and in particular to a human.

Terms such as "in need of treatment," "in need thereof," "benefit from such treatment," and the like, when used in the context of a subject being administered a pharmacologically active composition, generally refers to a judgment made by an appropriate healthcare provider that an individual or animal requires or will benefit from a specified treatment or medical intervention. Such judgments may be made based on a variety of factors that are in the realm of expertise of healthcare providers, but include knowledge that the individual or animal is ill, will be ill, or is at risk of becoming ill, as the result of a condition that may be ameliorated or treated with the specified medical intervention.

By "therapeutically effective amount" is meant an amount of a drug or pharmaceutical composition that will elicit at least one desired biological or physiological response of a cell, a tissue, a system, animal or human that is being sought by a researcher, veterinarian, physician or other caregiver.

The term "pharmacologically inert," as used herein, generally refers to a compound, additive, binder, vehicle, and the like, that is substantially free of any pharmacologic or "drug-like" activity.

In an embodiment, a method of treating cancer in a subject comprising administering to a subject who would benefit from such treatment a therapeutically effective amount of a pharmaceutical composition comprising a bisamidoxime. As described herein, bisamidoximes have been shown to be effective against a plurality of types of cancer, including but not limited to breast, lung, and colon cancer.

In an embodiment, a method of treating cancer in a subject comprising administering to a subject who would benefit from such treatment a therapeutically effective amount of a pharmaceutical composition comprising one, two or more bisamidoximes.

In some embodiment, bisamidoximes have the structure:

where W: is —$(CH_2)_2$—; —$(CH_2)_3$—; —$(CH_2)_4$—; or —$(CH_2)_3$—$N(CH_3)$—$(CH_2)_3$—; and
where Y is H, $C_1$-$C_6$ alkyl, or halogen. In a preferred embodiment, bisamidoximes have the structure above where Y is methyl. Specific examples of bisamidoximes include, but are not limited to JJMB 5, JJMB 6, JJMB 7, and JJMB 9:

In some embodiments, using a combination of two or more bisamidoximes produces a synergistic effect that enhances the effectiveness of the pharmaceutical composition. Synergistic effects have been observed in combinations of: JJMB5 and JJMB 9; JJMB5 and JJMB7; and JJMB7 and JJMB9.

In another embodiment, a method of treating cancer in a subject comprising administering to a subject who would benefit from such treatment a therapeutically effective amount of a pharmaceutical composition comprising an anticancer agent and one or more bisamidoximes. As described herein, a combination of a known anticancer agent and one or more bisamidoximes have been shown to be effective against a plurality of types of cancer, including but not limited to breast and colon cancer.

As used herein, the term "anticancer agent" refers to any agent that is administered to a subject with cancer for purposes of treating the cancer. Use of the subject bisamidoximes may be particularly advantageous and may enhance the effectiveness of the anticancer agent. Non-limiting examples of anticancer agents include topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; nucleoside mimetics (e.g., 5-fluorouracil, capecitibine, gemcitabine, fludarabine, cytarabine, mercaptopurine, thioguanine, pentostatin, and hydroxyurea); cell replication disrupters (e.g., paclitaxel, docetaxel, and related analogs; vincristine, vinblastin, and related analogs; thalidomide and related analogs (e.g., CC-5013 and CC-4047)); protein tyrosine kinase inhibitors (e.g., imatinib mesylate and gefitinib); antibodies which bind to proteins overexpressed in cancers and thereby downregulate cell replication (e.g., trastuzumab, rituximab, cetuximab, and bevacizumab); and other inhibitors of proteins or enzymes known to be upregulated, over-expressed or activated in cancers, the inhibition of which downregulates cell replication.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Nine novel bisamidoximes were tested for their potential to inhibit growth of malignant cell-lines in culture conditions. The bisamidoximes were synthesized according to the procedure set forth in the paper to Johnson et al. "Bisamidoximes: Synthesis and Complexation with Iron(III)", Aust. J. Chem. 2007, 60, 685-690, which is incorporated herein by reference.

Table 1 summarizes the results of the testing of four novel bisamidoximes. In Table 1, the various compounds listed were tested for induction of death in various malignant human cell lines and were compared to the commercial HAT inhibitor garcinol (0.2-500 µM). Specifically, Table 1 describes the summary of the growth inhibitory effect (in µM) of nine novel bisamidoximes on six malignant cell lines, as measured by MTS assay. MTS assay is a colorimetric based cytotoxicity assay that determines the number of viable cells. The numbers in the table represent Growth Inhibition $GI_{50}$ (±standard deviation), which is the concentration of the drug where 50% of the cells are killed. Garcinol, a known HAT inhibitor, was used as a positive control. The cell lines used were: HCT-116 (colorectal carcinoma), DU-145 (prostate carcinoma), SK-OV-3 (ovarian adenocarcinoma), HLF-a (lung epidermoid carcinoma), MCF-7 & MDA-MB-231 (breast adenocarcinoma) and NHDF (normal human dermal fibroblasts). The cells were treated with compounds JJMB 1-9 for 48 hrs (MCF-7 for 72 hrs) at various concentrations ranging from 0.2 µM to 500 µM. One-way ANOVA was performed to assess the differences between the groups. Differences in means between control and treatment groups were analyzed by post-hoc Dunnett's test, p<0.05. Data is reported as the mean ±SD, n =3. N-No inhibition; *—represents results from highly purified and more potent batches of the compounds. The compounds tested (JJMB5, JJMB6, JJMB7, and JJMB9) could efficiently kill several malignant cell-lines in concentration range of micromolars. (See Table 1). Furthermore, the compounds tested did not kill normal human dermal fibroblast cells (NHDF) at these concentrations, making them good candidates for continuing biochemical, pharmacological, and eventually medical studies. From these tests it is clear that the compounds affected several cells lines of the three major types of cancers: breast, lung, and colon.

Since the various potent amidoximes demonstrated a distinct pattern of cytotoxicity by killing different cell lines, it suggested that each of these compounds has a different mechanism of action. To further understand the mechanism of action of the four active compounds (JJMB5, JJMB6, JJMB7, and JJMB9), we performed several experiments that are summarized in Table 2. All the assays were performed on HCT-116 (a colorectal carcinoma), since all of the four specific potent drugs could induce death of these cells. The assays demonstrated that all the compounds induced apoptosis of cells (programed cell death), and all of them reduced the acetylation levels of core histones H3K9 and H4K5 in HCT-116 cells, which suggested that these compounds are HAT inhibitors. JJMB9 indeed inhibited the activity of a purified recombinant HAT—p300 in vitro (in a tube). Another HAT, GCN5, was not inhibited by any of the compounds. JJMB5, JJM6 and JJMB9 could reverse the activity of an HDAC inhibitor (TSA); thus the hyperacetylation induced by TSA could be reversed by these compounds.

This is another indication that the three compounds, JJMB5, JJMB6, and JJMB9 are HAT inhibitors. However, bisamidoxime JJMB7 could not reverse the TSA-induced hyperacetylation, indicating that it is not a HAT inhibitor. In accord with this notion, JJMB7 did not demonstrate inhibition of core histones acetylation in vivo prior to the onset of apoptosis, as opposed to JJMB5, JJMB6 and JJMB9. This result indicated that JJMB7 induces an indirect decrease of acetylation, not by inhibiting HATs, but by some alternative mechanism. The overall picture that emerges from the data presented in Tables 1 and 2 suggests that each of the four bisamidoximes that showed cell-death induction activity has a different mode of action.

Though the compounds induced apoptosis (programmed cell death) of several malignant lines, due to the fact that two different breast cancer cell lines, one estrogen receptor positive and the other estrogen receptor negative, were sensitive to the bisamidoximes, and due to the very high incidence of breast cancer, our approach in the experimental work was to focus on breast cancer. However, it should be understood that the results set forth herein are applicable to other forms of cancer, particularly colon cancer and lung cancer.

TABLE 1

Induction of death in malignant human cell lines by bisamidoximes (JJMB 5, 6, 7, and 9), and the commercial HAT inhibitor garcinol (0.2-500 µM)

| Cell Line | JJMB5 | JJMB6 | JJMB7 | JJMB9 | Garcinol |
| --- | --- | --- | --- | --- | --- |
| Colon (HCT-116) | 8.5* ± 2.5 | 17 ± 4 | 6.2* ± 2 | 16* ± 3.4 | 39 ± 8 |
| Lung (HLF-A) | 335 ± 4 | N | 275 ± 3 | 40 ± 7 | 27 ± 4 |
| Breast (MCF-7), 72 hours | 33.2* ± 6.0 | N | N | 8.5* ± 2.5 | 55 ± 7 |
| Breast (MDA-MB-231) | 125 ± 4 | N | 85 ± 3 | N | 44 ± 4 |
| Prostate (DU-145) | N | N | N | N | 55 ± 7 |
| Ovarian (SKOV-3) | N | N | N | N | 43 ± 5 |
| Normal (NHDF) | N | N | N | N | N |

TABLE 2

Comparison of various characteristics of the bisamidoximes that specifically killed malignant cells in culture

| ACTIVITY | JJMB5 | JJMB6 | JJMB7 | JJMB9 |
| --- | --- | --- | --- | --- |
| Induction of apoptosis in HCT-116 cells | + | + | + | + |
| Inhibition of histones H3K9 acetylation in HCT-116 cells | + | + | + | + |
| Inhibition of histones H4K5 acetylation in HCT-116 cells | + | + | + | + |
| Inhibition of histones H3K27 acetylation in HCT-116 cells | + | + | − | + |
| Inhibition of the HAT p300 in vitro | − | − | − | + |
| Inhibition of the HAT GCN5 in vitro | − | − | − | − |
| Reversion of HDAC-inhibitor-induced hyperacetylation | + | + | − | + |
| Inhibition of core histone acetylation in vivo prior to onset of apoptosis | + | + | − | + |
| Induction of G1/S arrest | − | + | + | + |
| Induction of G2/M arrest | + | − | − | − |

The efficacy of killing malignant cells in mice and slowing down the tumors or eradicating them can be indicative to these compounds' efficacy in humans. To check if the bisamidoximes are potent in mice, breast cancer cells were identified that could be implanted in female mice mammary fat pads. The identified cells were tested to see if they are sensitive to bisamidoximes in vitro (in tube/cell culture).

It was found that the murine mammary cancer cell line 4T1 (and also the EpH4 cells) was highly sensitive to three bisamidoximes that killed human breast cell lines (JJMB5, JJMB7, and JJMB9). The growth inhibition 50% ($GI_{50}$) of the various drugs on 4T1 cells were as follows: JJMB5—6.3±2.3 µM; JJMB7—14.7±6.3 µM; and JJMB9—33.3±2.4 µM. At the next stage, we needed to determine whether the mice would tolerate the drugs, or in other words, what would be the maximum tolerated dose (MTD) of each of the bisamidoximes. The three bisamidoximes JJMB5, JJMB7, and JJMB9, as well as a control group of only the vehicle (the solvent used to dissolve the drugs) were injected intraperitoneally (IP) to mice. The protocol included injection of the desired concentration of bisamidoxime over 5 consecutive days, two days of break, and another cycle of 5 successive days of injections. It was determined that the maximum tolerated doses in mice (BALB/c strain) were as follows: JJMB5—0.26 mg/kg; JJMB7—1.56 mg/kg; and JJMB9—0.78 mg/kg.

Figure 2:
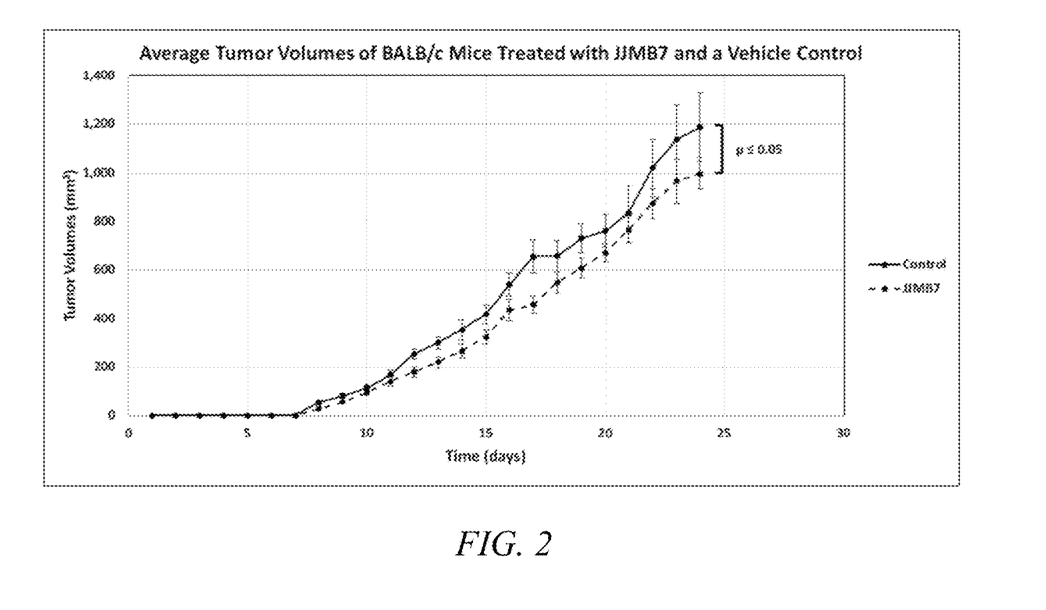
FIG. 2 depicts a graph of mammary tumor volumes in JJMB7 treated and untreated control BALB/c mice.

The bisamidoxime JJMB7 was studied to see if the compound can lower the rate of tumor growth and the number and size of metastases in mice. JJMB7, was found to significantly reduce the mammary carcinoma tumor volume when injected IP. FIG. 2 depicts a graph of mammary tumor volumes in JJMB7 treated and untreated control BALB/c mice. In the experiment, six-week-old BALB/c mice were implanted with 10,000 4T1 breast carcinoma cells in the mammary fat pad (MFP). The next day, 10 mice were injected IP with the maximum tolerated dose (MTD) of 1.56 mg/kg of JJMB7, and 10 control mice were injected with the vehicle alone. JJMB7 was administered for five consecutive days, followed by a two day break, and another five consecutive days of injections. Mice were weighed every day and observed for signs of pain and discomfort. Tumors were visible 7 days after implantation, and tumor dimensions were measured, and volumes were calculated until day-24, when mice were euthanized. A One-Way Repeated Measures ANOVA was performed to determine a statistical significance ($p \leq 0.05$).

In parallel to the in vivo testing, tests were performed to study the efficacy of various combinations of the bisamidoximes on killing human malignant cancer cells in culture. Since each of our four compounds being tested have a different mode of action, each of the compounds most likely have a different molecular target in the cells.

The results of various tests of combinations of bisamidoximes on malignant cancer cell lines are summarized in Table 3. Combination studies performed on human breast cancer cell line MCF-7 and human colon cancer cell line HCT 116 were measured by MTS assay. The cells were treated with novel bisamidoximes JJMB 5, 7, and 9, for 48 hours (72 hours for MCF-7), individually or in combination. Growth Inhibition ($GI_{50}$) was measured. *—Indicates a significant difference when the drugs were used in combination compared to when the drugs were used individually as determined by one-way ANOVA, $p \leq 0.05$.

TABLE 3

Combination studies of novel bisamidoximes on malignant cell lines

| Cell Line | Amidoxime | Growth Inhibition ($GI_{50}$) in uM |
|---|---|---|
| MCF-7 | JJMB5 | 28.2 ± 7.1 |
| | JJMB9 | 5.3 ± 2.7 |
| | JJMB5 & JJMB9 | 5.1 ± 3.3* |
| HCT-116 | JJMB5 | 20.4 ± 3.6 |
| | JJMB9 | 20.9 ± 3.5 |
| | JJMB5 & JJMB9 | 9.4 ± 2.2* |
| | JJMB5 | 22.4 ± 1.1 |
| | JJMB7 | 15.5 ± 5.6 |
| | JJMB5 & JJMB7 | 5.7 ± 1.4* |
| | JJMB7 | 25.2 ± 1.7 |
| | JJMB9 | 22.4 ± 4.4 |
| | JJMB7 & JJMB9 | 7.2 ± 1.5* |

TABLE 3-continued

Combination studies of novel bisamidoximes on malignant cell lines

| Cell Line | Amidoxime | Growth Inhibition ($GI_{50}$) in uM |
|---|---|---|
| 4T1 | JJMB5 | 7.8 ± 3.2 |
| | JJMB9 | 26.1 ± 5.9 |
| | JJMB5 & JJMB9 | 3.4 ± 0.8 |
| | JJMB5 | 8.2 ± 0.1 |
| | JJMB7 | 7.1 ± 0.8 |
| | JJMB5 & JJMB7 | 3.2 ± 0.7* |
| | JJMB7 | 8.0 ± 0.6 |
| | JJMB9 | 30.2 ± 2.0 |
| | JJMB7 & JJMB9 | 4.2 ± 0.6* |

The results described in Table 3 demonstrate that combinations of JJMB5 and JJMB9, JJMB5 and JJMB7, or JJMB7 and JJMB9 were more efficient in killing the colon cancer cells HCT-116 (lower $GI_{50S}$) than using each of the bisamidoximes alone. The same combinations were also more efficient in inducing the death of the murine mammary carcinoma cells 4T1.

The results of various tests of combinations of bisamidoximes with cisplatin on malignant cancer cell lines are summarized in Table 4.

TABLE 4

Combination studies of cisplatin and novel bisamidoximes on human malignant cell lines

| Cell Line | Amidoxime | Growth Inhibition (GI50) in μM |
|---|---|---|
| MCF-7 | JJMB5 | 33.2 ± 6.0 |
| | Cisplatin | 48.5 ± 6.5 |
| | JJMB5 & Cisplatin | 17.2 ± 3.8* |
| | JJMB9 | 8.5 ± 2.5 |
| | Cisplatin | 40.8 ± 2.6 |
| | JJMB9 & Cisplatin | 5 ± 1.2* |
| HCT-116 | JJMB5 | 19.3 ± 2.4 |
| | Cisplatin | 68.6 ± 8.5 |
| | JJMB5 & Cisplatin | 7.9 ± 0.5* |
| | JJMB7 | 16.2 ± 2.0 |
| | Cisplatin | 73 ± 9.0 |
| | JJMB7 & Cisplatin | 6.2 ± 1.0* |
| | JJMB9 | 16 ± 3.4 |
| | Cisplatin | 66.3 ± 8.4 |
| | JJMB9 & Cisplatin | 8.1 ± 1.0* |

Combination studies of bisamidoximes and cisplatin were performed on human breast cancer cell line MCF-7, human colon cancer cell line HCT-116, and murine mammary malignant cell lines measured by MTS assay. The cells were treated with novel bisamidoximes JJMB 5, 7, and 9, for 48 hours (72 hours for MCF-7), individually or in combination with cisplatin. Growth Inhibition ($GI_{50}$) was measured. *—Indicates a significant difference when the drugs were used in combination with cisplatin compared to when the drugs were used individually as determined by one-way ANOVA, $p \leq 0.05$.

The results summarized in Table 4 show that the combination of the commonly used chemotherapeutic agent cisplatin and JJMB5, and cisplatin and JJMB9, were more efficient in killing the human breast cancer cells MCF-7. The combination of JJMB5, JJMB7, or JJMB9 with cisplatin was also more efficient in killing the colon carcinoma cells HCT-116. In addition, it appears that the bisamidoximes JJMB5, JJM7, and JJMB9 were more efficient individually than the commercially available and widely used cisplatin.

Figure 3:
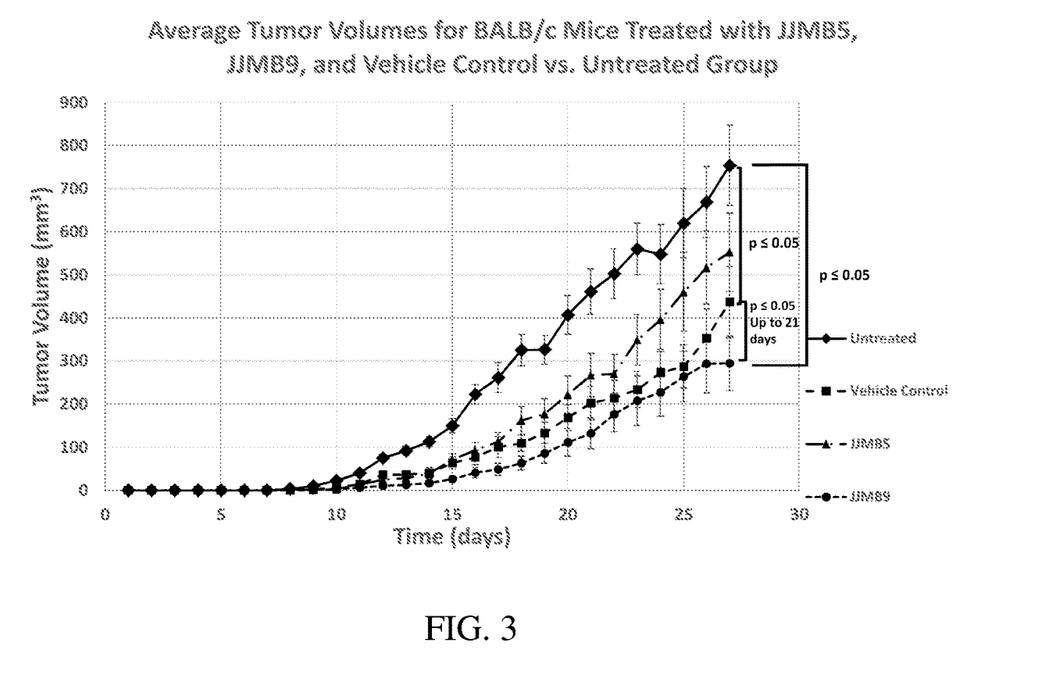
FIG. 3 is a graph depicting the effect of compound JJMB9 on breast cancer tumor volume.

FIG. 3 shows that compound JJMB9 significantly reduced the breast cancer tumor volume up to day 21 since the implantation of the malignant cells (mouse mammary carcinoma). The murine mammary carcinoma 4T1 cells were implanted in the mammary fat pad of BALB/c female mice (10,000 cells per mice) and a day later we started a protocol of two 5-day cycles (with 2 days break) of chemotherapy delivered IP. The amidoximes were delivered at their MTD level—JJMB5 with 0.26 mg/kg, and JJMB9 with 0.78 mg/kg. One-Way Repeated-Measure ANNOVA was performed to show the significance ($p \leq 0.05$, $n=10$).

Figure 4:
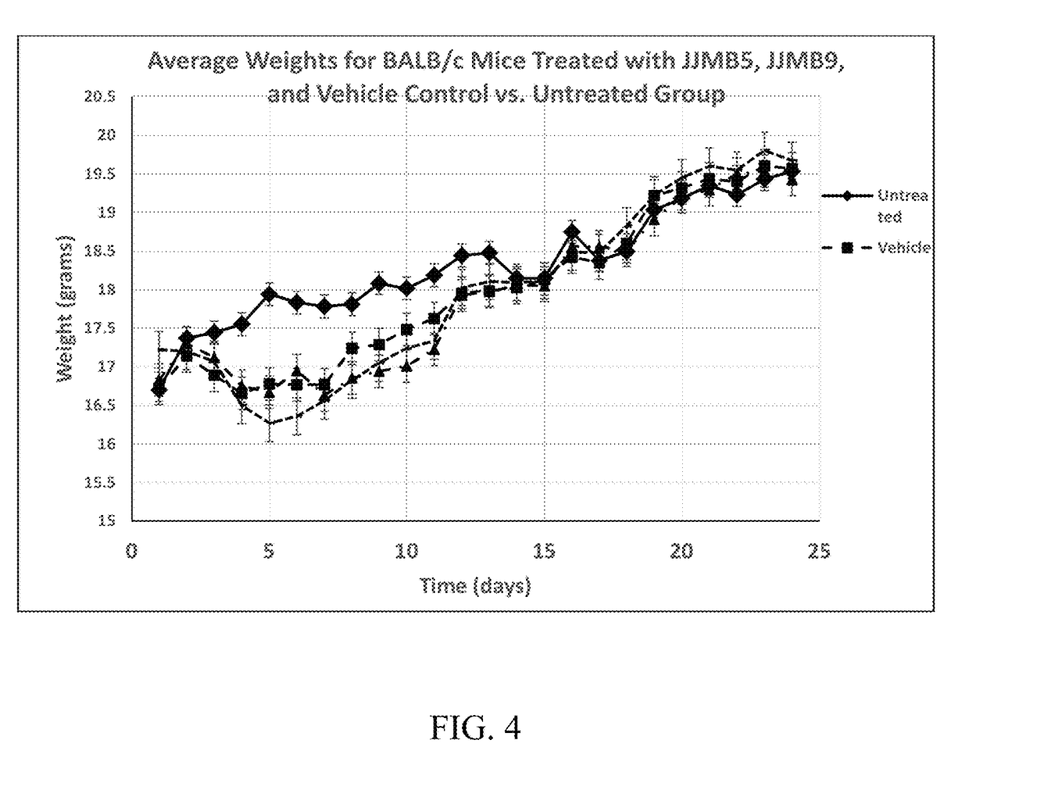
FIG. 4 depicts the daily weight of mice during treatment with compound JJMB9.

FIG. 4 shows the daily weight of mice during this experiment, indicating that though the drug-injected mice lost some weight during the first days of injection, they later bounced back to the normal weight range shown by the untreated control mice group. The untreated mice were also transplanted with 4T1 cells, but they were not injected the vehicle or one of the drugs.

Figure 5:
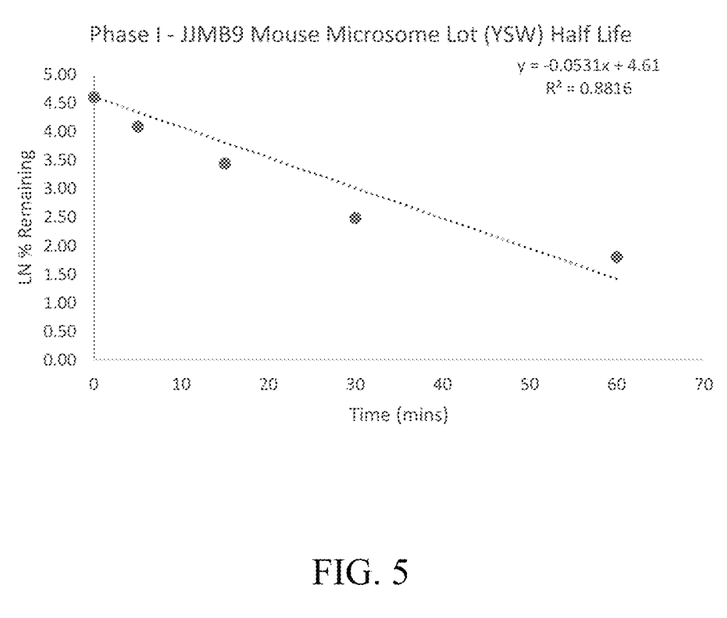
FIG. 5 depicts the effect of compound JJMB9 on Mouse Liver Microsomes.

FIG. 5 demonstrates our study with Mouse Liver Microsomes which revealed the t1/2 of JJMB9 to be 13 minutes.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method of treating colon cancer, breast cancer, or lung cancer in a subject comprising administering to a subject who would benefit from such treatment a therapeutically effective amount of a pharmaceutical composition comprising one or more bisamidoximes, wherein the one or more biamidoximes are selected from the group of compounds consisting of JJMB 5, JJMB6, JJMB 7, and JJMB 9:

JJMB5

JJMB6

JJMB7

2. The method of claim 1, wherein the pharmaceutical composition comprises two or more bisamidoximes.

3. The method of claim 2, wherein the pharmaceutical composition comprises JJMB5 and JJMB 9.

4. The method of claim 2, wherein the pharmaceutical composition comprises JJMB5 and JJMB7.

5. The method of claim 2, wherein the pharmaceutical composition comprises JJMB7 and JJMB9.

6. The method of claim 1, wherein the cancer is breast cancer.

7. The method of claim 1, wherein the cancer is lung cancer.

8. The method of claim 1, wherein the cancer is colon cancer.

9. A method of treating colon cancer, breast cancer, or lung cancer in a subject comprising administering to a subject who would benefit from such treatment a therapeutically effective amount of a pharmaceutical composition comprising an anticancer agent and one or more bisamidoximes, wherein the one or more biamidoximes are selected from the group of compounds consisting of JJMB 5, JJMB6, JJMB 7, and JJMB 9:

JJMB5

JJMB6

-continued

JJMB7

JJMB9

10. The method of claim 9, wherein the anticancer agent is cisplatin.

11. The method of claim 9, wherein the pharmaceutical composition comprises JJMB5.

12. The method of claim 9, wherein the pharmaceutical composition comprises JJMB7.

13. The method of claim 9, wherein the pharmaceutical composition comprises JJMB9.

14. The method of claim 9, wherein the cancer is breast cancer.

15. The method of claim 9, wherein the cancer is lung cancer.

16. The method of claim 9, wherein the cancer is colon cancer.

* * * * *

UNITED STATES PATENT AND TRADEMARK OFFICE
CERTIFICATE OF CORRECTION

PATENT NO. : 10,758,501 B2  
APPLICATION NO. : 16/149892  
DATED : September 1, 2020  
INVENTOR(S) : Michael Bergel et al.

Page 1 of 1

It is certified that error appears in the above-identified patent and that said Letters Patent is hereby corrected as shown below:

In the Claims

Claim 1, Column 15, Line 55, please delete "biamidoximes" and replace with "bisamidoximes".
Claim 9, Column 16, Line 46, please delete "biamidoximes" and replace with "bisamidoximes".

Signed and Sealed this
Thirteenth Day of October, 2020

Andrei Iancu
*Director of the United States Patent and Trademark Office*